(12) United States Patent
Jagannath et al.

(10) Patent No.: US 10,328,063 B2
(45) Date of Patent: Jun. 25, 2019

(54) METHOD OF WOUND HEALING

(71) Applicant: CONNEXIOS LIFE SCIENCES PVT. LTD, Bengaluru (IN)

(72) Inventors: M. R. Jagannath, Bengaluru (IN); M. V. Venkataranganna, Bengaluru (IN); Somesh Baggavalli, Bengaluru (IN); Anup Oommen Mammen, Bengaluru (IN)

( * ) Notice: Subject to any disclaimer, the term of this patent is extended or adjusted under 35 U.S.C. 154(b) by 0 days.

(21) Appl. No.: 15/751,499

(22) PCT Filed: Aug. 11, 2016

(86) PCT No.: PCT/IN2016/050270
§ 371 (c)(1),
(2) Date: Feb. 9, 2018

(87) PCT Pub. No.: WO2017/025988
PCT Pub. Date: Feb. 16, 2017

(65) Prior Publication Data
US 2018/0221356 A1     Aug. 9, 2018

(30) Foreign Application Priority Data
Aug. 11, 2015 (IN) .......................... 4178/CHE/2015

(51) Int. Cl.
| | |
|---|---|
| *A61K 31/439* | (2006.01) |
| *C07D 209/04* | (2006.01) |
| *A61P 17/02* | (2006.01) |
| *A61K 9/00* | (2006.01) |
| *A61K 47/06* | (2006.01) |
| *A61K 47/10* | (2017.01) |
| *A61K 47/12* | (2006.01) |
| *A61K 47/14* | (2017.01) |
| *A61K 47/22* | (2006.01) |
| *A61K 47/34* | (2017.01) |
| *A61K 47/46* | (2006.01) |

(52) U.S. Cl.
CPC .......... *A61K 31/439* (2013.01); *A61K 9/0014* (2013.01); *A61K 47/06* (2013.01); *A61K 47/10* (2013.01); *A61K 47/12* (2013.01); *A61K 47/14* (2013.01); *A61K 47/22* (2013.01); *A61K 47/34* (2013.01); *A61K 47/46* (2013.01); *A61P 17/02* (2018.01)

(58) Field of Classification Search
CPC ........................... C07D 209/04; A61K 31/439
USPC ........................................... 548/469; 514/295
See application file for complete search history.

(56) References Cited

FOREIGN PATENT DOCUMENTS

| | | | |
|---|---|---|---|
| WO | 2004112779 A1 | | 12/2004 |
| WO | 2013/111150 | * | 8/2013 |
| WO | 2013111150 A1 | | 8/2013 |

OTHER PUBLICATIONS

International Search Report and Written Opinion for PCT/IN2016/050270, dated Jan. 18, 2017.
Jong-Kyung Youm et al, "Local blockade of glucocorticoid activation reverses stress- and glucocorticoid-induced delays in cutaneous wound healing," Wound Repair and Regeneration., Sep. 8, 2013, pp. 715-722, vol. 21, No. 5.
Ana Tiganescu et al., "11β Hydroxysteroid dehydrogenase blockade prevents age-induced skin structure and function defects," The Journal of Clinical Investigation, Jul. 2013, pp. 3,051-3,060, vol. 123, No. 7.
Gary R. Small et al., "Preventing local regeneration of glucocorticoids by 11β-hydroxysteroid dehydrogenase type 1 enhances angiogenesis," Proceedings of the National Academy of Sciences, Aug. 23, 2005, pp. 12,165-12,170, vol. 102, No. 34.
Ana Tiganescu et al., "Increased glucocorticoid activation during mouse skin wound healing," Journal of Endocrinology, Jan. 24, 2014, pp. 51-61, vol. 221, No. 1, Bioscientifica Ltd.

\* cited by examiner

*Primary Examiner* — Niloofar Rahmani
(74) *Attorney, Agent, or Firm* — Hauptman Ham, LLP

(57) ABSTRACT

The present invention relates to a method of treating a wound, comprising administering to a subject in need thereof a therapeutically effective amount of an aza adamantane compound according to Formula (I), or a pharmaceutically acceptable salt, thereof.

20 Claims, 8 Drawing Sheets

CNX-010-640

***

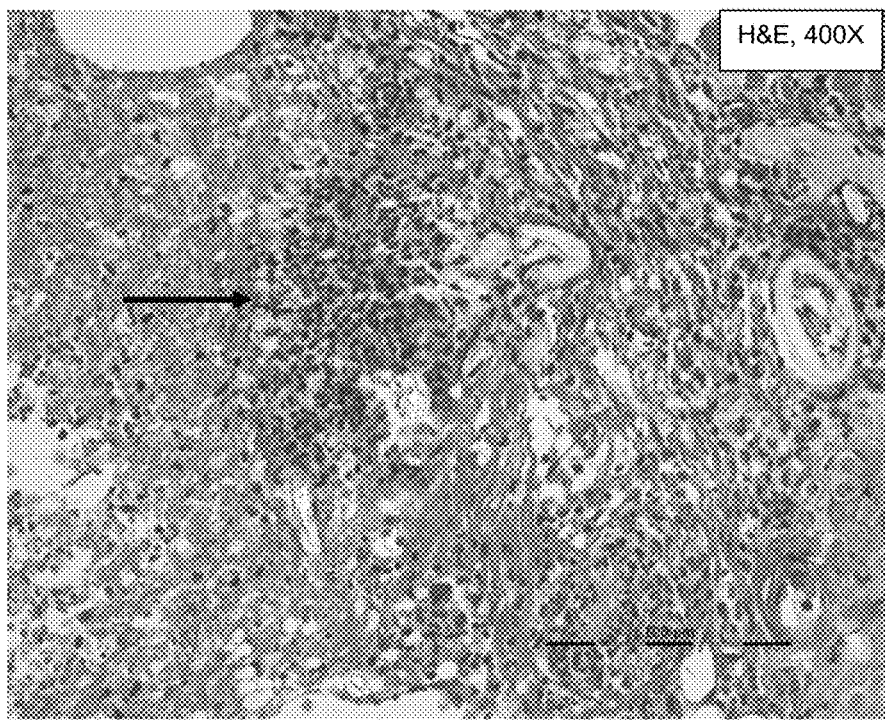
Figure 6: G2 (HFD + VersaPro control): polymorphonuclear cell infiltration – moderate (arrow)
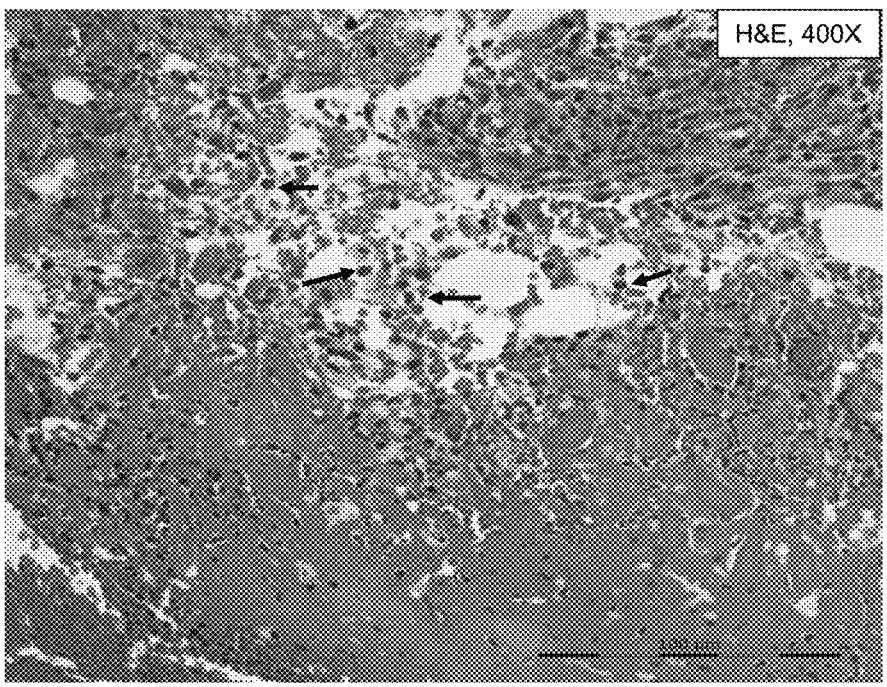
Figure 7: G3 (HFD + 0.5% CNX-010-640 formulated cream): polymorphonuclear cell infiltration – mild (arrows)

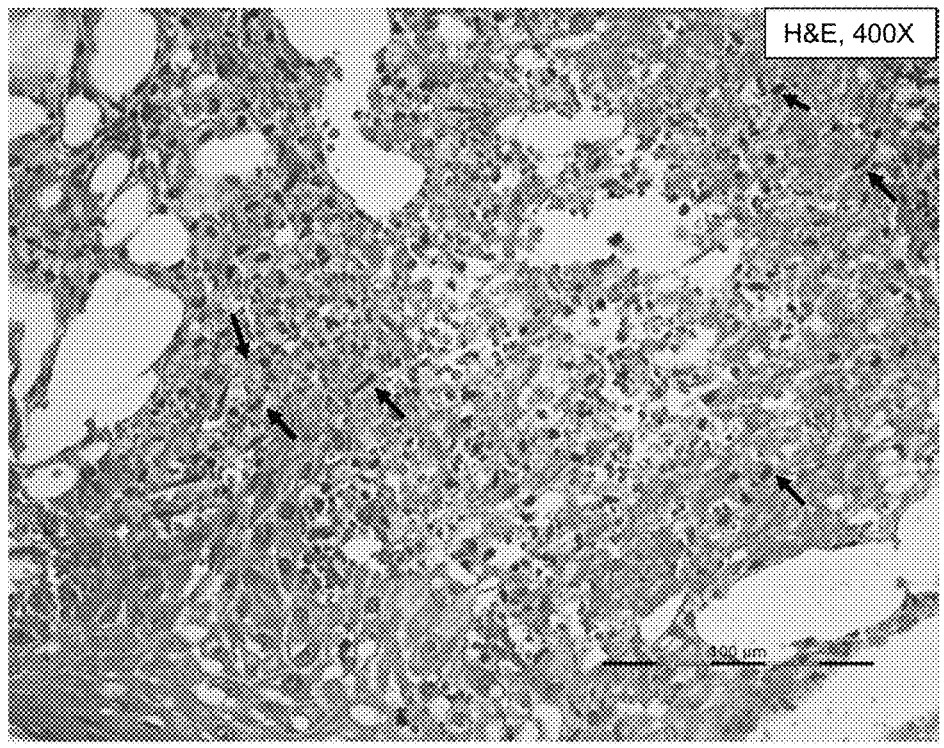
Figure 8: G2 (HFD + VersaPro control):
few fibroblasts at the site of healing (arrows)
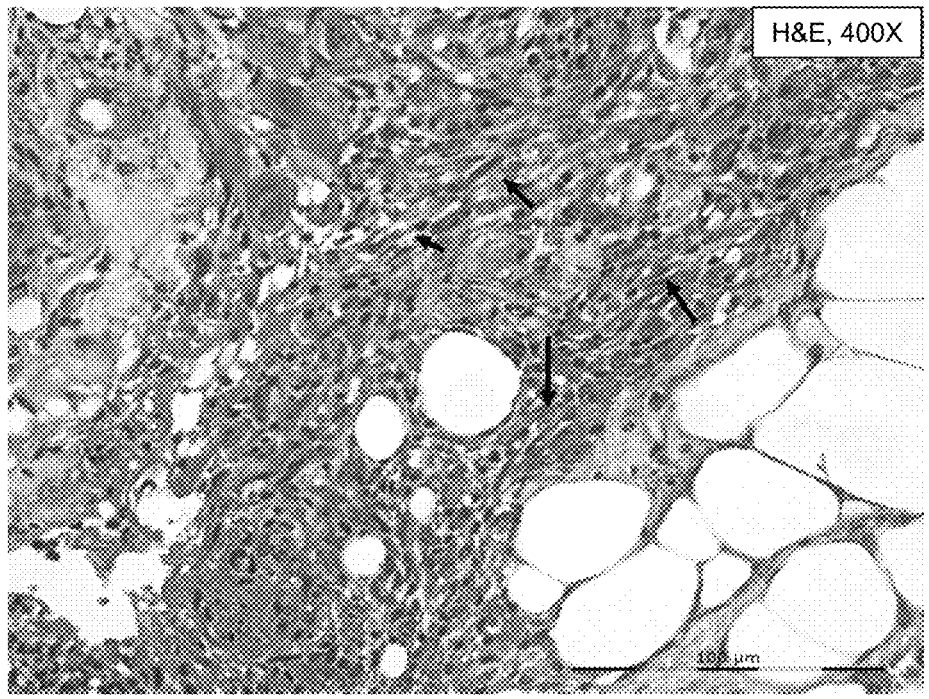
Figure 9: G3 (HFD + 0.5% CNX-010-640 formulated cream):
abundant fibroblasts at the site of healing (arrows)

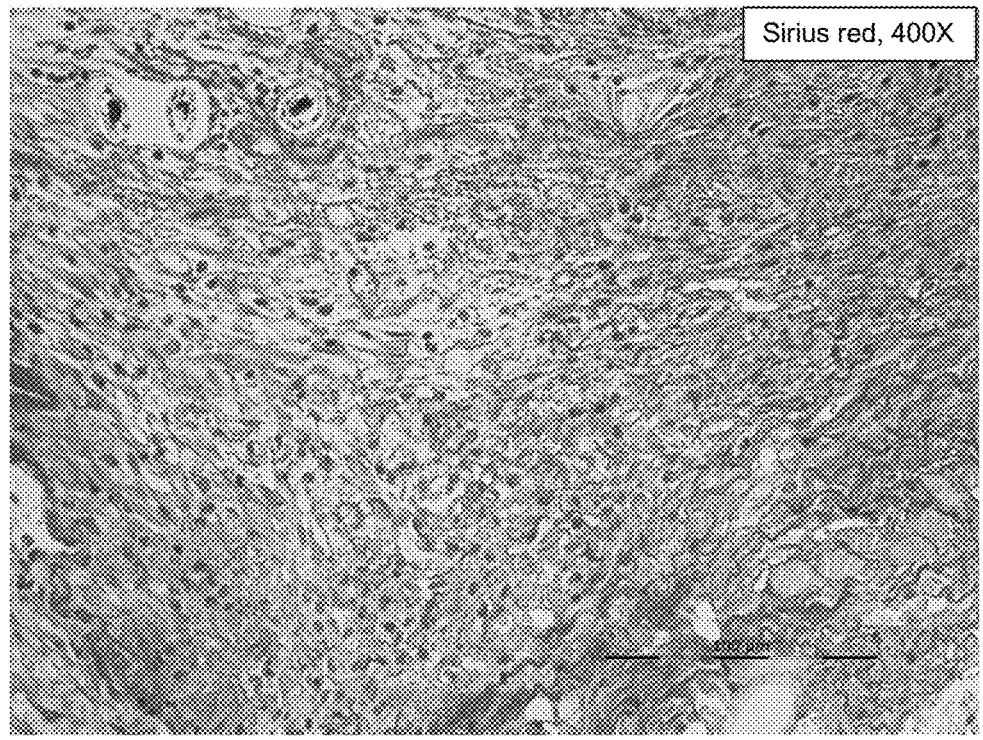
Figure 10: G2 (HFD + VersaPro control): collagen deposition – mild
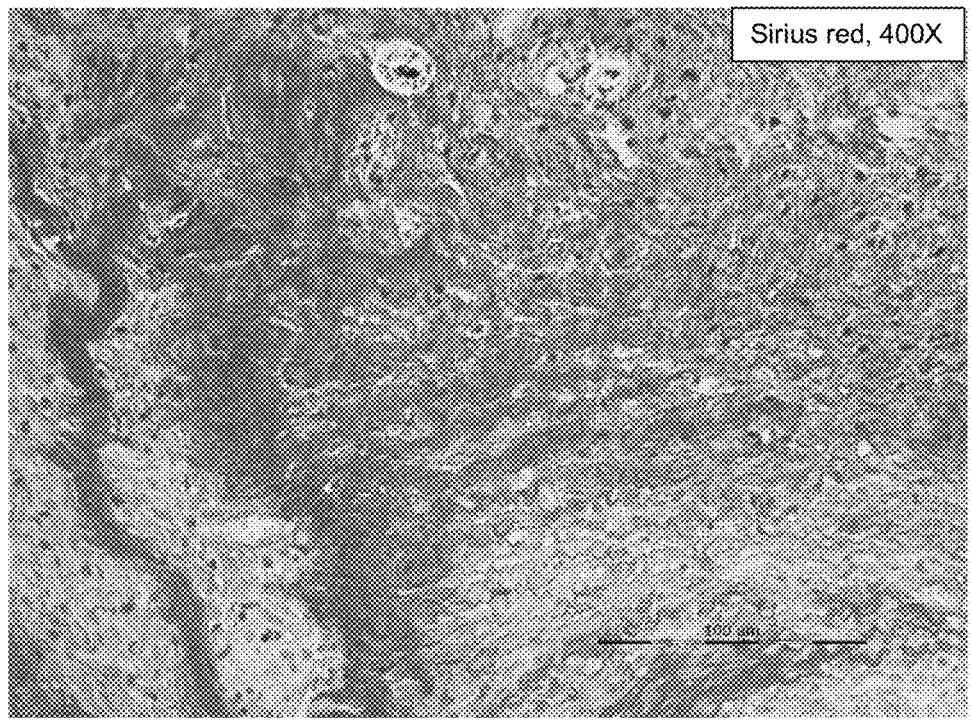
Figure 11: G3 (HFD + 0.5% CNX-010-640 formulated cream): collagen deposition – moderate

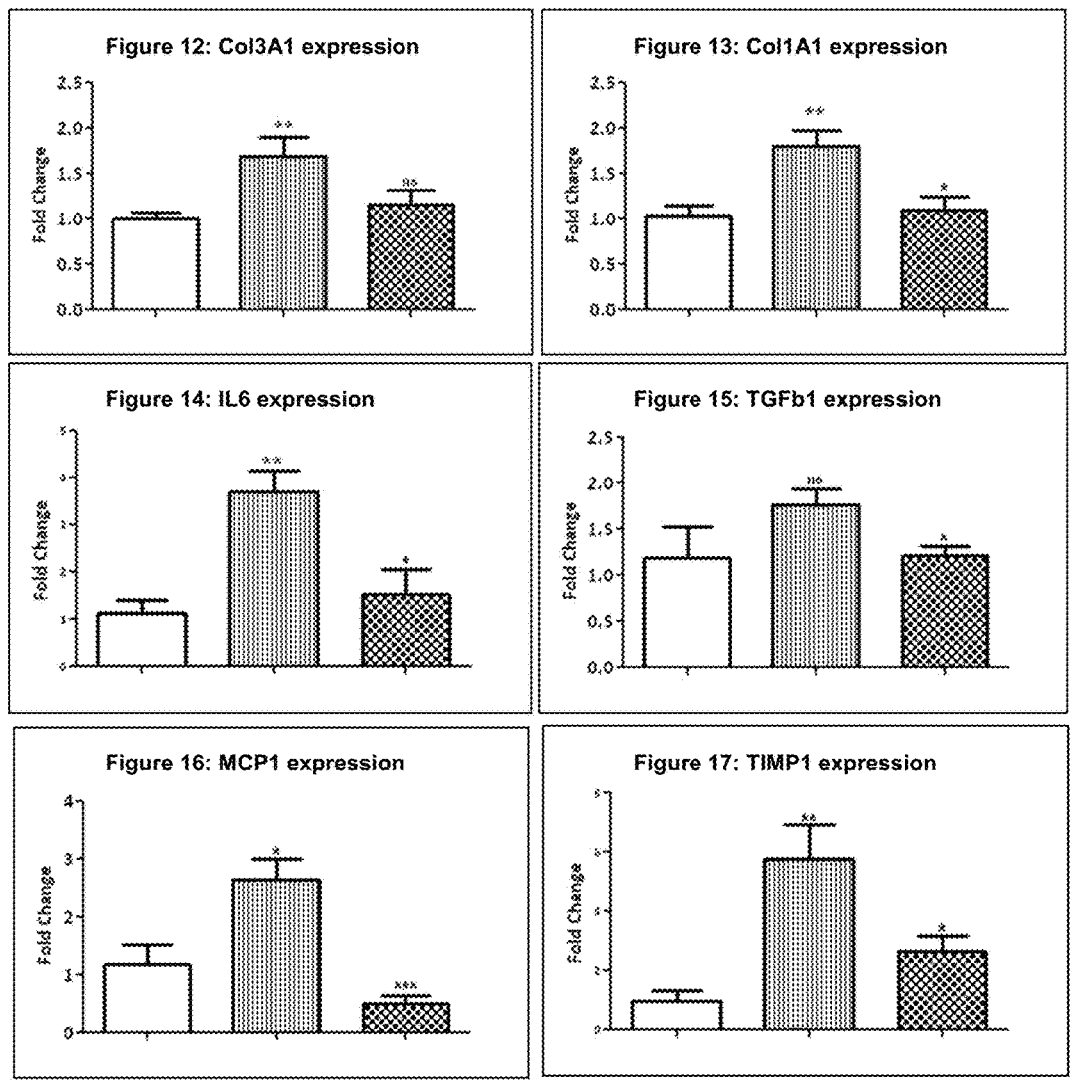
Figures 12 to 17: relative levels of gene expression
☐ Lean   ▥ HFD   ▩ HFD+ Compound

METHOD OF WOUND HEALING

CROSS REFERENCE

This application claims priority from Indian Provisional Patent Application No. 4178/CHE/2015 filed 11 Aug. 2015, the contents of which should be understood to be incorporated into this specification by this reference.

TECHNICAL FIELD

The present invention relates to methods of treating a wound with an aza adamantane derivative according to Formula (I), or a pharmaceutically acceptable salt thereof. In addition, the invention relates to use of an aza adamantane derivative according to Formula (I), or a pharmaceutically acceptable salt thereof in the manufacture of a medicament for the treatment of a wound, an aza adamantane derivative according to Formula (I), or a pharmaceutically acceptable salt thereof for use in treating a wound, and pharmaceutical compositions containing an aza adamantane derivative according to Formula (I), or a pharmaceutically acceptable salt thereof for use in treating a wound.

BACKGROUND OF INVENTION

A wound is defined as an injury to a part of the body. Wounds may be inflicted on a subject in any number of ways, such as by mechanical injury, burns or surgery, and have been sustained on humans and animals since time immemorial.

The process of wound healing typically undergoes four distinct phases: blood clotting (also known as hemostasis); inflammation; growth of new tissue (also known as proliferation); and remodeling of tissue (also known as maturation). The treatment of wounds, such as those mentioned above and especially those resulting from excisions or incisions, is one of the primary goals of any medical practitioner. Traditional methods of treating wounds to promote healing include keeping the wound clean and protecting the wound from harmful bacterial contamination. There have also been a number of methods developed that include application to the wound of a wound healing agent to facilitate wound healing. If the healing process can be accelerated in any way, this would be of great benefit to both a patient and a medical practitioner.

Hydroxysteroid dehydrogenases are enzymes that catalyze the dehydrogenation of hydroxysteroids. It has previously been described that 11β-hydroxysteroid dehydrogenases (HSD-11β or 11β-HSD) are a family of oxidoreductase enzymes that catalyze the conversion of cortisone to active cortisol (a glucocorticoid, GC). There are two known isoforms of 11β-hydroxysteroid dehydrogenases in humans, known as type 1 and type 2.

Glucocorticoid excess may affect skin integrity, inducing thinning and impaired wound healing. GCs may also induce a flattening of the normally undulating rete ridges at the dermal-epidermal junction leading to altered mechanical properties and delayed wound healing. Without wishing to be bound by theory, it is believed that inhibition of 11β-HSD may lead to improved wound healing in a patient.

The inventors have now surprisingly found that a specific aza adamantane compound, or a pharmaceutically acceptable salt thereof, disclosed in WO 2013/111150, filed on 21 Dec. 2012, has beneficial effects in the treatment of wounds. The entire contents of the above disclosure are incorporated herein by reference.

SUMMARY OF INVENTION

In one aspect the present invention provides a method of treating a wound, comprising administering to a subject in need thereof a therapeutically effective amount of a compound of Formula (I), or a pharmaceutically acceptable salt thereof:

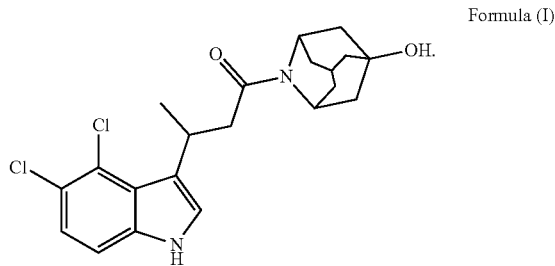 [SMILES: CC(CC(=O)N1C2CC3CC1CC(O)(C3)C2)c1c[nH]c2ccc(Cl)c(Cl)c12]

Formula (I)

In another aspect, the present invention provides the use of a compound of Formula (I) as defined above, or a pharmaceutically acceptable salt thereof, in the manufacture of a medicament for the treatment of a wound in a subject.

In another aspect, the present invention provides a compound of Formula (I) as defined above, or a pharmaceutically acceptable salt thereof, for use in treating a wound in a subject.

In another aspect, the present invention provides an agent for use in treating a wound in a subject, wherein the agent comprises a compound according to Formula (I) as defined above, or a pharmaceutically acceptable salt thereof.

In another aspect, the present invention provides a pharmaceutical composition for use in treating a wound in a subject, comprising a compound according to Formula (I) as defined above, or a pharmaceutically acceptable salt thereof, and a pharmaceutically acceptable diluent, excipient or carrier.

In one embodiment, the pharmaceutical composition comprises from 0.1 to 2% (w/w) of a compound of Formula (I), or a pharmaceutically acceptable salt thereof and from 99.9 to 98% (w/w) of a carrier. In one embodiment, the pharmaceutical composition comprises from 0.1 to 1% (w/w) of a compound of Formula (I), or a pharmaceutically acceptable salt thereof and from 99.9 to 99% (w/w) of a carrier. In one embodiment the pharmaceutical composition comprises about 0.5% (w/w) of the compound of Formula (I), and about 99.5% (w/w) of a carrier.

In one embodiment the pharmaceutical composition comprises 0.1 to 2% (w/w) of a compound of Formula (I), or a pharmaceutically acceptable salt thereof; one or more emollients at about 5 to about 10% (w/w); one or more surfactants at about 10 to about 15% (w/w); one or more humectants at about 1 to about 10% (w/w); one or more preservatives at about 1 to about 5% (w/w); one or more antioxidants at about 0.1 to about 2% (w/w); and a solvent making the remaining balance up to 100% (w/w).

In one embodiment the one or more emollients is selected from the group consisting of heavy liquid paraffin, kokum butter and cetyl alcohol. In one embodiment the one or more surfactants is selected from the group consisting of glyceryl monostearate, stearic acid, polyethylene glycol, cetostearyl alcohol and ethylene glycol monostearate. In one embodiment the one or more humectants is glycerine. In one embodiment the one or more preservatives is selected from the group consisting of phenoxy ethanol, potassium sorbate and sodium benzoate. In one embodiment the one or more antioxidants is vitamin E. In one embodiment the solvent is water.

In one embodiment the pharmaceutical composition comprises 0.5% (w/w) of a compound of Formula (I), or a pharmaceutically acceptable salt thereof, heavy liquid paraffin—2.5% (w/w); glyceryl mono stearate—1.85% (w/w); stearic acid—2.0% (w/w); kokum butter—2.0% (w/w); polyethylene glycol—5.0% (w/w); glycerine—5.0% (w/w); cetostearyl alcohol—2.5% (w/w); cetyl alcohol—2.0% (w/w); ethylene glycol monostearate—1.0% (w/w); phenoxy ethanol—0.5% (w/w); potassium sorbate—0.5% (w/w); sodium benzoate—0.5% (w/w); vitamin E—0.5% (w/w); and purified water—73.65% (w/w).

BRIEF DESCRIPTION OF DRAWINGS

FIG. 6 depicts cells from a wound in a diabetes-induced mouse after treatment with the control cream, VersaPro (no active agent), showing moderate polymorphonuclear cell infiltration.

FIG. 7 depicts cells from a wound in a diabetes-induced mouse after treatment with VersaPro cream containing CNX-010-640 at 0.5% by weight of the total weight, showing mild polymorphonuclear cell infiltration.

FIG. 8 shows the degree of fibroblast proliferation from a wound in a diabetes-induced mouse after treatment with the control cream, VersaPro (no active agent).

FIG. 9 shows the degree of fibroblast proliferation from a wound in a diabetes-induced mouse after treatment with VersaPro containing CNX-010-640 at 0.5% by weight of the total weight.

FIG. 10 shows the degree of collagen deposition from a wound in a diabetes-induced mouse after treatment with the control cream, VersaPro (no active agent).

FIG. 11 shows the degree of collagen deposition from a wound in a diabetes-induced mouse after treatment with VersaPro containing CNX-010-640 at 0.5% by weight of the total weight.

FIGS. 12 to 17 show the relative levels of gene expression from non-diabetes control mice, diabetes-induced control mice, and diabetes-induced mice treated with CNX-010-640.

DETAILED DESCRIPTION

Figure 1:
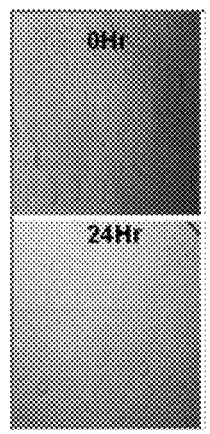
FIG. 1 shows results of an in vitro scratch assay at t=0 h and after 24 h, after treatment with the aza adamantane compound according to Formula (I), or a pharmaceutically acceptable salt thereof. CNX 640 is the compound of Formula (I) as detailed above.

In this specification a number of terms are used which are well known to a skilled addressee. Nevertheless for the purposes of clarity a number of terms will be defined.

It is understood that included with the compound of Formula (I) are isomeric forms including diastereoisomers, enantiomers, where applicable. It is also understood that some isomeric forms such as diastereomers, enantiomers, and geometrical isomers can be separated by physical and/or chemical methods and by those skilled in the art. For those compounds where there is the possibility of geometric isomerism the applicant has drawn the isomer that the compound is thought to be although it will be appreciated that the other isomer may be the correct structural assignment. Where the structural isomer is not known or where the compound is thought to be a mixture of the two isomers the attachment to the double bond is shown as a wavy line.

The compound of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula (I) is intended to cover, where applicable, solvated as well as unsolvated forms of the compound. Thus, each formula includes the compound having the indicated structure, including the hydrated as well as the non-hydrated forms.

The term "pharmaceutically acceptable salt" refers to a salt that retains the desired biological activity of the above-identified compounds, and include pharmaceutically acceptable acid addition salts and base addition salts. Suitable pharmaceutically acceptable acid addition salts of the compound of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propanoic, succinic, glycolic, gluconic, lactic, malic, tartaric, citric, fumaric, maleic, alkyl sulfonic, and arylsulfonic. In a similar vein base addition salts may be prepared by ways well known in the art using organic or inorganic bases. Examples of suitable organic bases include simple amines such as methylamine, ethylamine, triethylamine and the like. Examples of suitable inorganic bases include NaOH, KOH, and the like. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formula.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The term "wound" refers to an injury to a body tissue. Examples of wounds which can be treated in accordance with the present invention are: abrasions, aseptic wounds, burns, contused wounds, incised wounds (incisions), excised wounds (excisions), lacerated wounds, non-penetrating wounds (i.e. wounds in which there is no disruption of the skin but there is injury to underlying structures), open wounds, penetrating wounds, perforating wounds, puncture wounds, septic wounds, sores, subcutaneous wounds and ulcers. Examples of sores are bed sores, cancer sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, symptomatic ulcer, trophic ulcer, tropical ulcer, venereal ulcer, e.g. caused by gonorrhoea (including urethritis, endocervicitis and proctitis). Conditions related to wounds or sores which may be successfully treated according to the invention are anthrax, tetanus, gas gangrene, scalatina, erysipelas, sycosis barbae, folliculitis, impetigo contagiosa, or impetigo bullosa, etc. Therefore as mentioned above, in the present context the term "wound" encompasses the term "ulcer", "lesion", "sore" and "infarction".

The wound may also be due to a disorder (such as diabetes), an infectious lesion, surgery, a puncture, a chronic wound, or a scar. The wound may be a chronic skin ulceration, a sore, a dermal wound, or an epidermal wound. The wound may be due to destructive wound inflammation, delayed or impaired healing, or disturbed tissue regeneration. The wound may be located internally or externally of a subject.

The compound according to Formula (I), or a pharmaceutically acceptable salt thereof has the ability to inhibit 11β-HSD1. The ability to inhibit 11β-HSD1 may be a result of the compound acting directly and solely on the 11β-HSD1 to modulate/potentiate biological activity. However, it is understood that the compound, or a pharmaceutically acceptable salt thereof may also act at least partially on other factors associated with 11β-HSD1 activity.

The inhibition of 11β-HSD1 may be carried out in any of a number of ways known in the art. For example if inhibition of 11β-HSD1 in vitro is desired an appropriate amount of the compound, or a pharmaceutically acceptable salt thereof may be added to a solution containing the 11β-HSD1. In circumstances where it is desired to inhibit 11β-HSD1 in a mammal, the inhibition of the 11β-HSD1 typically involves administering the compound, or a pharmaceutically acceptable salt thereof to a mammal containing the 11β-HSD1.

Accordingly the compound according to Formula (I), or a pharmaceutically acceptable salt thereof may find a multiple number of applications in which its ability to inhibit 11β-HSD1 enzyme of the type mentioned above can be utilised.

In one aspect, the compound, or a pharmaceutically acceptable salt thereof for use in the present invention may be delivered along with one or more other active compounds, such as those typically used for treatment of wounds.

Examples of agents typically used for treating wounds include orally or topically applied agents (such as pentoxifylline and iloprost), analgesics, antibodies, anti-coagulants, anti-inflammatories, anti-microbials (such as iodine-based preparations, silver-releasing preparations, broad spectrum anti-microbial agents and systemic antibiotics), anti-mycotic agents (such as polyenes and azoles), anti-septics, anti-tuberculotic drugs, calcium antagonists (such as diltiazem and nifedipine), colchicine, corticosteroids, cytokines, cytotoxic drugs, glyceryl trinitrate, honey, hydrogen peroxide or hydrogen peroxide generators, immunosuppressive drugs, nicotine, NSAIDs, phenytoin, protease inhibitors, retinoids, vasoconstrictors, and zinc (topical or oral preparations).

In one embodiment the compound according to Formula (I), or a pharmaceutically acceptable salt thereof, medicament, agent or pharmaceutical composition can be administered by a route selected from the group consisting of oral, parenteral, intraarterial, intravenous, intracavity, intramuscular, intraperitoneal, intrapleural, intrathecal, intravesical, transdermal, sublingual, rectal, transbuccal, intranasal, liposomal, via inhalation, vaginal, intraoccular, via local delivery (for example by catheter or stent), subcutaneous, intraadiposal, intraarticular, and intrathecal.

In one embodiment the compound according to Formula (I), or a pharmaceutically acceptable salt thereof, medicament, agent or pharmaceutical composition can be administered topically to the site of the wound. Topically means to the skin or mucous membranes where the wound is located, and/or to the surrounding areas which may be affected by the wound.

Wound dressings may incorporate or have applied thereto the aza adamantane compound according to the invention. Dressings have a number of purposes, depending on the type, severity and position of the wound, although all purposes are focused towards promoting recovery and preventing further harm from the wound. Key purposes of a dressing are to seal the wound and expedite the clotting process, to soak up blood, plasma and other fluids exuded from the wound, to provide pain relieving effect (including a placebo effect), to debride the wound, to protect the wound from infection and mechanical damage, and to promote healing through granulation and epithelialization.

A typical (sterile) dressing can be made of an alginate, a fibrous material, a film, a foam, a semi-solid gel, a hydrocolloid, a hydrogel, granules or beads, a pad, a gauze, or a fabric. More particularly, sterile dressings can be made of, for example, silicone, a fibrin/fibrinogen matrix, polyacrylamide, PTFE, PGA, PLA, PLGA, a polycaprolactone or a hyaluronic acid. Dressing may further be described as compression dressings, adherent dressings and non-adherent dressings.

In another aspect, there is provided a kit comprising the above compound and instructions which comprise one or more forms of information selected from the group consisting of: indicating a disease state for which the compound is to be administered, storage information for the compound, dosing information, and instructions regarding how to administer the compound. In one aspect, the kit comprises the compound in a multiple dose form.

In yet another aspect there is provided an article of manufacture comprising the above compound and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the composition. In another variation, the article of manufacture comprises the compound in a multiple dose form.

Administration of the compound according to Formula (I), or a pharmaceutically acceptable salt thereof to a subject can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose.

In using the compound of the invention it can be administered in any form or mode which makes the compound bioavailable. One skilled in the art of preparing formulations can readily select the proper form and mode of administration depending upon the particular characteristics of the compound, the wound to be treated, the stage of healing of the wound to be treated and other relevant circumstances. We refer the reader to Remingtons Pharmaceutical Sciences, 19$^{th}$ edition, Mack Publishing Co. (1995) for further information.

The compound according to Formula (I), or a pharmaceutically acceptable salt thereof can be administered alone or in the form of a pharmaceutical composition in combination with a pharmaceutically acceptable carrier, diluent or excipient. The compound of the invention, while effective itself, is typically formulated and administered in the form of its pharmaceutically acceptable salt as this form is typically more stable, more easily crystallised and has increased solubility.

In one embodiment, the present invention relates to a pharmaceutical composition comprising the aza adamantane compound, or a pharmaceutically acceptable salt thereof according to the invention and a pharmaceutically acceptable diluent, excipient or carrier. In one embodiment the composition may be adapted for topical administration.

The compound is, however, typically used in the form of pharmaceutical compositions which are formulated depending on the desired mode of administration. As such in some embodiments the present invention provides a pharmaceutical composition including a compound of Formula (I), or a pharmaceutically acceptable salt thereof and a pharmaceutically acceptable carrier, diluent or excipient. The compositions are prepared in manners well known in the art.

Topical compositions typically comprise the active ingredient with suitable carriers (such as semi-synthetic glycerides and/or synthetic glycerides), cellulose derivatives, chelating agents (such as citrate, EGTA or EDTA), emollients, emulsifiers, excipients, fatty alcohols, glycerol, hydrocarbon oils or waxes, hydrogenated oils, lanolin and derivatives, paraffins, polyethylene glycols, polyhydric alcohols/esters, silicon oils, sterols, and/or other waxes (such as beeswax and derivatives and vegetable waxes). Such additives are well known in the art of formulation science.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compound according to Formula (I), or a pharmaceutically acceptable salt thereof may be used or administered in combination with one or more additional drug(s) for the treatment of the disorder/diseases mentioned. The components can be administered in the same formulation or in separate formulations. If administered in separate formulations the compound of the invention, or a pharmaceutically acceptable salt thereof may be administered sequentially or simultaneously with the other drug(s).

In addition to being able to be administered in combination with one or more additional drugs, the compound of the invention, or a pharmaceutically acceptable salt thereof may be used in a combination therapy. When this is done the compounds are typically administered in combination with each other. Thus the compound of the invention, or a pharmaceutically acceptable salt thereof may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compound according to Formula (I), or a pharmaceutically acceptable salt thereof can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound, or a pharmaceutically acceptable salt thereof is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compound according to Formula (I), or a pharmaceutically acceptable salt thereof can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compound, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compound, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound according to Formula (I), or a pharmaceutically acceptable salt thereof include powders, patches, sprays, ointments and inhalants. The active compound, or a pharmaceutically acceptable salt thereof is mixed under sterile conditions with a pharmaceutically acceptable carrier and any needed preservatives, buffers, or propellants which may be required.

The aza adamantane compound according to Formula (I), or a pharmaceutically acceptable salt thereof may be used either neat or in the form of a medicament, an agent, or a pharmaceutical composition and may be contacted with the wound using a wound dressing; in a balm, a cream, a gel, a liniment, a lotion, an ointment, a paste, a rub or a salve; in a topical spray; in a powder; by injection locally or regionally to the wound; in a topical liquid; or with a suture.

The balm, cream, gel, liniment, lotion, ointment, paste, rub or salve may be comprised of any readily available carrier, as will be appreciated by one of ordinary skill in the art, as well as the aza adamantane compound according to Formula (I), or a pharmaceutically acceptable salt thereof. It may come in a number of different forms with a number of different ingredients. We refer the reader to The Chemistry and Manufacture of Cosmetics, $3^{rd}$ edition, Allured Publishing Corporation (2002) for further information.

A carrier is any material that is suitable for application to a wound, which can be used as a base to mix with the aza adamantane compound according to Formula (I), or a pharmaceutically acceptable salt thereof. An example of a suitable carrier is VersaPro cream base, which is available from Medisca. Other companies also sell carriers, also known as cream bases, for compounding with active ingredients, such as Perfect Potion, Sydney Essential Oil Co., and Bulk Apothecary amongst many others.

A carrier may be comprised of one or more emollients, one or more surfactants, one or more lubricants, one or more preservatives, one or more antioxidants, and a solvent.

An emollient is a mixture of chemical agents specially designed to make the external layers of the skin (epidermis) softer and more pliable. It increases the skin's hydration (water content) by reducing evaporation. Naturally occurring skin lipids and sterols, as well as artificial or natural components may be part of the composition of commercial skin emollients (moisturizers). Examples of emollients include but are not limited to the following: paraffin, liquid paraffin, heavy liquid paraffin, kokum butter, cetyl alcohol, fats and oils such as lanolin, shea butter, cocoa butter, mineral oil, lanolin, petrolatum, beeswax, squalene, coconut, jojoba, sesame, almond, and other plant oils, olive oil (oleic acid), and triethylhexanoin.

As stated above, a carrier may comprise one or more emollients. If an emollient is present in the carrier, it may typically be present in a range from about 1 to about 20% (w/w), along with the aza adamantane compound according to Formula (I), or a pharmaceutically acceptable salt thereof, other ingredients, and with a solvent making the remaining balance up to 100% (w/w). One or more emollients can be present, with the total weight of the one or more emollients preferably being in the range of about 5 to about 10% (w/w).

A surfactant or "surface active agent" is a molecule that contains both a hydrophobic group or portion of the molecule and a hydrophilic group or portion. A hydrophobic group is a group that "dislikes water" and therefore will be unlikely to be soluble in water. A synonym for hydrophobic is lipophilic, which means "fat loving", and throughout this specification these two terms may be used interchangeably. In contrast, a hydrophilic group is one that "likes water" and therefore will be likely to be soluble in water. A synonym for hydrophilic is lipophobic, which means "fat fearing", and throughout this specification these two latter terms may also be used interchangeably. Examples of surfactants include but are not limited to the following: glyceryl monostearate, stearic acid, polyethylene glycol, cetostearyl alcohol, ethylene glycol monostearate, sodium dodecyl sulfate, sodium stearate, 4-(5-dodecyl) benzenesulfonate, sodium or ammonium lauryl or laureth sulfate, sodium methyl cocoyl taurate, sodium lauroyl or cocoyl sarcosinate, cocomidopropyl betaine, triethanolamine (TEA) compounds, diethanolamine (DEA) compounds, monoethanolamine (MEA) compounds, and dioctyl sulfosuccinate, As stated above, a carrier may comprise one or more surfactants. If a surfactant is present in the carrier, it may typically be present in a range from about 1 to about 20% (w/w), along with the aza adamantane compound according to Formula (I), or a pharmaceutically acceptable salt thereof, other ingredients, and with a solvent making the remaining balance up to 100% (w/w). One or more surfactants can be present, with the total weight of the one or more surfactants preferably being in the range of about 10 to about 15% (w/w).

A humectant is a hygroscopic substance used to keep things moist; it is the opposite of a desiccant. It is often a molecule with several hydrophilic groups, most often hydroxyl groups; however, amines and carboxyl groups, sometimes esterified, can be encountered as well. Its affinity to form hydrogen bonds with molecules of water is the crucial trait. They are used in many products, including food, cosmetics, medicines and pesticides. Examples of humectants include but are not limited to the following: triethylene glycol, tripropylene glycol, propylene glycol, polypropylene glycols, glycerine (also known as glycerin or glycerol), sorbitol (sugar alcohol), hexylene, butylene glycol, urea, and collagen.

As stated above, a carrier may comprise one or more humectants. If a humectant is present in the carrier, it may typically be present in a range from about 1 to about 20% (w/w), along with the aza adamantane compound according to Formula (I), or a pharmaceutically acceptable salt thereof, other ingredients, and with a solvent making the remaining balance up to 100% (w/w). One or more humectants can be present, with the total weight of the one or more humectants preferably being in the range of about 1 to about 10% (w/w).

A preservative is a substance that prevents decomposition by microbial growth or by undesirable chemical changes. Examples of preservatives include but are not limited to the following: phenoxy ethanol, sorbic acid, sodium sorbate, potassium sorbate, benzoic acid, sodium benzoate, potassium benzoate, benzyl alcohol, phenethyl alcohol, and hydroxybenzoate and derivatives.

As stated above, a carrier may comprise one or more preservatives. If a preservative is present in the carrier, it may typically be present in a range from about 1 to about 20% (w/w), along with the aza adamantane compound according to Formula (I), or a pharmaceutically acceptable salt thereof, other ingredients, and with a solvent making the remaining balance up to 100% (w/w). One or more preservatives can be present, with the total weight of the one or more preservatives preferably being in the range of about 1 to about 5% (w/w).

An antioxidant is a molecule that inhibits the oxidation of other molecules. Oxidation is a chemical reaction that can produce free radicals, leading to chain reactions that may damage cells. Antioxidants terminate these chain reactions. Examples of antioxidants include but are not limited to the following: vitamin A and other carotenoids, vitamin C and other ascorbates such as ascorbic acid and sodium ascorbate, butylated hydroxytoluene, butylated hydroxyanisole, tertiary butylhydroquinone, gallic acid and sodium gallate, and vitamin E and other tocopherols.

As stated above, a carrier may comprise one or more antioxidants. If an antioxidant is present in the carrier, it may typically be present in a range from about 0.1 to about 5% (w/w), along with the aza adamantane compound according to Formula (I), or a pharmaceutically acceptable salt thereof, other ingredients, and with a solvent making the remaining balance up to 100% (w/w). One or more antioxidants can be present, with the total weight of the one or more antioxidants preferably being in the range of about 0.1 to about 2% (w/w).

A solvent is a substance used to provide a liquid or creamy consistency to a balm, cream, gel, liniment, lotion, ointment, paste, rub or salve. The solvent interacts with the carrier, which may be comprised of one or more emollients, one or more surfactants, one or more lubricants, one or more preservatives, and one or more antioxidants to form a composition that can be applied to a wound. Examples of solvents include but are not limited to the following: water (purified water), alcohols such as ethanol, and glycols. Preferably the solvent is water.

In one embodiment the present invention provides use of an aza adamantane compound of Formula (I), or a pharmaceutically acceptable salt thereof, in the manufacture of a medicament for the treatment of a wound in a subject. In one embodiment the wound is an incision or an excision. In one embodiment, the medicament is adapted to be administered topically to the site of the wound. In one embodiment the medicament is in the form of a balm, a cream, a gel, a liniment, a lotion, an ointment, a paste, a rub or a salve.

In one embodiment the present invention provides a compound for use in treating a wound in a subject, wherein the compound is an aza adamantane compound according to Formula (I), or a pharmaceutically acceptable salt thereof. In one embodiment the wound is an incision or an excision. In one embodiment the compound is administered topically to the site of the wound. In one embodiment the compound is administered in the form of a balm, a cream, a gel, a liniment, a lotion, an ointment, a paste, a rub or a salve.

In one aspect, the present invention provides an agent for use in treating a wound in a subject, wherein the agent comprises an aza adamantane compound according to Formula (I), or a pharmaceutically acceptable salt thereof, or a pharmaceutically acceptable salt thereof. In one embodiment the wound is an incision or an excision. In one embodiment the agent is adapted to be administered topically to the site of the wound. In one embodiment the agent is in the form of a balm, a cream, a gel, a liniment, a lotion, an ointment, a paste, a rub or a salve.

The amount of compound according to Formula (I), or a pharmaceutically acceptable salt thereof administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the compound administered, the mode of administration, the bioavailability of the preparation administered, the dose regime selected, the use of other medications and other relevant circumstances.

In one embodiment the composition will comprise a compound according to Formula (I), or a pharmaceutically acceptable salt thereof in a range from about 0.001 to 5% by weight of the total weight of the composition in the form of a cream based formulation. A more preferred dosage will be in the range from 0.01 to 5%, more preferably from 0.1 to 5%, even more preferably 0.1 to 2%, by weight of the total weight of the composition in the form of a cream based formulation. In one embodiment the composition will comprise a compound of Formula(I) of from 0.1 to 2%, more preferably from 0.1 to 1%, even more preferably about 0.5% by weight of the total weight of the composition in the form of a cream based formulation. A suitable dose can be administered in multiple sub-doses per day.

EXAMPLES

[1] The formulations of the various embodiments may be prepared using the methods as described below, employing the techniques available in the art using starting materials that are readily available.

[2] The preparation of particular formulations of the embodiments is described in detail in the following examples, but the artisan will recognize that the procedures described may be readily adapted to prepare a number of other agents of the various embodiments. For example, the preparation of non-exemplified formulations may be successfully performed by modifications apparent to those skilled in the art, e.g. by modifying the order of addition of ingredients, by changing to other suitable ingredients known in the art, or by making routine modifications such as increasing or decreasing the temperature at various stages of the preparation. Alternatively, other formulations disclosed herein or known in the art will be recognized as having applicability for preparing other formulations of the various embodiments.

[3] Ingredients useful for preparing formulations may be obtained or prepared according to techniques known in the art.

[4] The symbols, abbreviations and conventions in the processes, schemes, and examples are consistent with those used in the contemporary scientific literature. Specifically but not meant as limiting, the following abbreviations may be used in the examples and throughout the specification:

11β-HSD or HSD-11β (11β-hydroxysteroid dehydrogenase)
11β-HSD1 (11β-hydroxysteroid dehydrogenase—type 1)
$CDCl_3$ (deuterated chloroform)
cDNA (complementary DNA)
$CHCl_3$ (chloroform)
DCM (dichloromethane)
DMF (N,N-dimethylformamide)
DMSO (dimethylsulfoxide)
EDTA (ethylenediaminetetraacetic acid)
EGTA (ethylene glycol tetraacetic acid)
EtOAc (ethyl acetate)
EtOH (ethanol)
g (grams)
GC (glucocorticoid)
h (hours)
HCl (hydrochloric acid)
HDF (human dermal fibroblast)
HFD (high fat diet)
Hz (Hertz)
$K_2CO_3$ (potassium carbonate)
L (liters)
MeOH (methanol)
mg (milligrams)
MHz (megahertz)
min (minutes)
mL (milliliters)
mM (millimolar)
mol (moles)
$Na_2SO_4$ (sodium sulfate)
NSAID (non-steroidal anti-inflammatory drug)
PBS (phosphate-buffered saline)
PCR (polymerase chain reaction)
PGA (poly (glycolic acid))
PLA (poly (lactic acid))
PLGA (poly (lactic-co-glycolic acid))
psi (pounds per square inch)
PTFE (polytetrafluoroethylene)
RM (reaction mixture)
RNA (ribonucleic acid)
RT (room temperature)
SEM (standard error of the mean)
THF (tetrahydrofuran)
TLC (thin layer chromatography)

[5] Unless otherwise indicated, all temperatures are expressed in ° C. (degree centigrade). All preparations were conducted at room temperature unless otherwise mentioned. All ingredients used are commercially available. VersaPro™ Cream Base is also commercially available from Medisca.

Example 1

The compound of Formula (I) was synthesized as outlined in Synthetic Schemes 1 and 2:

Synthesis of 4-oxotricyclo [3.3.1.1$^{3,7}$] dec-2-yl methanesulfonate (Intermediate-1)

A 1000 mL RB flask fitted with magnetic stirrer was charged with methanesulfonic acid (416.0 g, 4328.8 mmol) and Starting Material-1 (50.0 g, 333 mmol). To this sodium azide (23.0 g, 351 10 mmol) was added portion wise for 2 hours. Then reaction mixture was stirred at 20-25° C. for 3 days. Upon completion of the reaction (reaction monitored by TLC), reaction mixture was quenched with ice-water (3000 mL) and extracted with ethyl acetate (1000×3 mL). The organic layer was washed with brine solution, dried over anhydrous sodium sulfate and concentrated to give title Intermediate-1 (54.0 g, yield=66%).

Synthesis of bicyclo[3.3.1]non-6-ene-3-carboxylic acid (Intermediate-2)

A 2000 mL RB flask fitted with magnetic stirrer was charged with 1200 mL of ethanol and Intermediate-1 (54.0 g, 221.3 mmol). Potassium hydroxide (84.0 g, 150 mmol) was further added to this reaction mixture followed by addition of 950 mL of water. The reaction mixture was stirred at 110° C. for 12 hours. After completion of the reaction (reaction was monitored by TLC), reaction mixture was concentrated under vacuum. The resulted crude material was acidified with 1N HCl (pH=2) and extracted with ethyl acetate (250×3 mL). The organic layer was washed with brine solution, dried over anhydrous sodium sulfate and concentrated 10 to give Intermediate-2 (32.0 g, yield=88%).

Synthesis of methyl bicyclo[3.3.1]non-6-en-3-ylcarbamate (Intermediate-3)

A 500 mL RB flask fitted with magnetic stirrer under nitrogen atmosphere charged with toluene (100 mL), Intermediate-2 (16.0 g, 96 mmol) and DPPA (28.8 g, 105 mmol). Reaction mixture was cooled to 0° C., and then triethylamine (15.4 g, 143.9 mmol) was added. The reaction mixture was stirred at room temperature for 1 hour. Then reaction mixture was heated at 80° C. for 8 h and 12 h at room temperature. To this 100 mL of methanol was added and refluxed for 12 hours. After the reaction, it was concentrated under vacuum. Obtained crude was extracted with ethyl acetate. The organic layer was washed with 1N HCl, Saturated NaHCO$_3$ solution, brine solution and was then dried over anhydrous sodium sulfate and concentrated. Crude material was purified by silica gel column chromatography eluting with 6% of EtOAc in to give Intermediate-3 (8.0 g, yield=42%).

Synthesis of methyl 2-azatricyclo [3.3.1.1$^3$]decane-2-carboxylate (Intermediate-4)

A 100 mL RB flask fitted with magnetic stirrer was charged with 50 mL of dichloromethane and Intermediate-3 (5.0 g, 25.6 mmol). To this reaction mixture, triflouromethane sulfonic acid (19.2 g, 125.2 mmol) was added at 0° C. The reaction mixture was then stirred at room temperature for 12 hours. After completion of reaction, the reaction mixture was quenched with water and extracted with dichloromethane. The organic layer was washed with saturated sodium bicarbonate solution, brine solution and the reaction mass was dried over anhydrous sodium sulfate and was concentrated to give Intermediate-4 (4.3 g, yield=86%).

Synthesis of 2-azatricyclo [3.3.1.1$^{3,7}$]decane (Intermediate-5)

A 50 mL pressurized seal tube fitted with magnetic stirrer was charged with Intermediate-4 (3.0 g, 15 mmol) in HCl containing 1,4-Dioxane (20 mL). Then the reaction mixture was stirred at 90° C. for 8 hours. After completion of the reaction (reaction was monitored by LCMS) it was concentrated followed by trituration with mixture of hexane:ether (1:1) to give Intermediate-5 (3.0 g, yield=100%).

Synthesis of tert-butyl 5-hydroxy-2-azatricyclo [3.3.1.1$^{3,7}$]decane-2-carboxylate (Intermediate-6)

A 250 mL RB fitted with magnetic stirrer was charged with Intermediate 5 (3.0 g, 21.6 mmol), concentrated nitric acid (30 mL), and H$_2$SO$_4$ (5 mL). The reaction mixture was stirred at 80° C. for 12 hours. Upon completion of the reaction (reaction was monitored by LC-MS) reaction mixture was quenched with water and basified with sodium carbonate. The aqueous layer was washed with DCM (100 mL) and resulting aqueous layer was diluted with THF (200 mL) and cooled to 0° C. The pH of the mixture was adjusted to basic using Triethyl amine (5 mL). To this reaction mixture Boc-anhydride (6.0 g, 27.52 mmol) was added. The resulting mixture was stirred at room temperature for 12 hours. Upon completion of the reaction (reaction was monitored by LC-MS) reaction mixture was extracted with Ethyl acetate (100 mL×3). Combined organic layer was washed with water and brine and the reaction mass was dried over sodium sulfate. Organic layer was concentrated to obtain a crude intermediate which was then purified by silica gel column chromatography eluting with 40% of EtOAc to give Intermediate-6 (2.5 g, yield=50%).

Synthesis of 2-azatricyclo [3.3.1.1$^{3,7}$]decan-5-ol (Intermediate-7)

A 100 mL RB flask fitted with magnetic stirrer was charged with Intermediate-6 (5.5 g, 21.5 mmol) in DCM (30 mL). The reaction mixture thus formed was cooled to 0° C. to which trifluoroacetic acid (7.4 g, 65.2 mmol) was added and stirred for 4 hours. After completion of the reaction (reaction was monitored by LCMS) the reaction mixture was concentrated followed by trituration with mixture of hexane: ether (1:1) to give Intermediate-7 (3.4 g, yield=100%).

3-(4,5-Dichloro-1H-indol-3-yl)-1-(5-hydroxy-2-azatricyclo[3.3.1.1$^{3,7}$]dec-2-yl)butan-1-one, Formula (I)

Synthetic Scheme 2

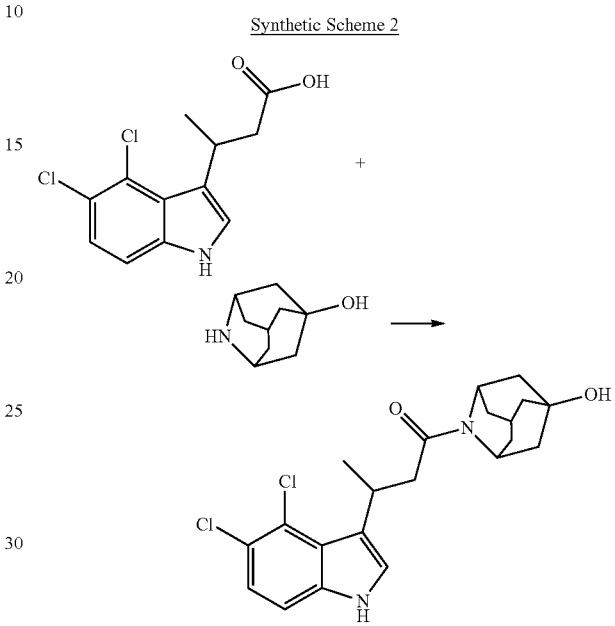

Starting Material (0.2 mmol) was added to Intermediate-7 (0.2 mmol) in dichloromethane (DCM), followed by the addition of 1-ethyl-3-(3-dimethylaminopropyl) carbodiimide hydrochloride (EDCl) (0.26 mmol) and 1-hydroxybenztriazole (HOBt) (0.23 mmol). The reaction mixture was cooled to 0° C. and was maintained at the same temperature for 30 minutes. Further, triethylamine (0.93 mmol) was added to the reaction mixture, and the resulting solution was stirred at room temperature for 15 hours. The reaction mass was then diluted with equal ratio of DCM and water, and was washed with 1N HCl solution followed by NaHCO$_3$ and brine solution. The organic layer was separated and dried over anhydrous sodium sulfate. The crude product was obtained by evaporating the organic layer under reduced pressure and was purified by silica gel column using DCM: MeOH as eluent to obtain the compound of Formula (I). $^1$H NMR (300 MHz, CDCl$_3$): δ 8.18 (br s, 1H), 7.10-7.13 (d, 2H), 7.06-7.07 (d, 1H), 5.00 (br s, 1H), 4.24 (br s, 1H), 4.04-4.07 (m, 1H), 2.78-2.84 (m, 1H), 2.37-2.47 (dd, 1H), 2.24-2.26 (m, 1H), 1.73-1.78 (m, 3H), 1.61-1.65 (m, 7H), 1.35-1.38 (d, 3H). LC-MS: (M+H)$^+$=407.1; HPLC purity=99.28%.

Example 2

A compound according to Formula (I) at 0.5% by weight of the total weight of the composition in the form of a cream based formulation was prepared according to the following:

Cream based composition for 100 gm:

| | |
|---|---|
| 1) Heavy Liquid Paraffin | 2.5 g |
| 2) Glyceryl Mono Stearate | 1.85 g |

| | |
|---|---|
| 3) Stearic acid | 2.0 g |
| 4) Kokum butter | 2.0 g |
| 5) Poly ethylene Glycol | 5.0 g |
| 6) Glycerin | 5.0 g |
| 7) Cetostearyl alcohol | 2.5 g |
| 8) Cetyl alcohol | 2.0 g |
| 9) Ethylene Glycol Monostearate | 1.0 g |
| 10) Phenoxy ethanol | 0.5 g |
| 11) Potassium sorbate | 0.5 g |
| 12) Sodium benzoate | 0.5 g |
| 13) Vitamin E | 0.5 mL |
| 14) Purified water | 73.65 mL |

Example 3

99.5 g of VersaPro™ Cream Base, a commercially available cream base was used with 0.5 g of the compound according to Formula (I).

Example 4

Results

In Vitro Scratch Assay

Human Dermal Fibroblast cells (HDF) cells were seeded in 24 well plates (25000 cells/mL) in 1 mL of growth media (Media-106, Gibco) and allowed to grow for 24 h at 37° C. and 5% $CO_2$. A small linear scratch was created in the confluent monolayer by gently scraping with sterile p200 pipette tips (care was taken during scratching process to ensure universal size and distant was made for all samples). Cells were extensively rinsed with PBS to remove cellular debris before adding the media with different treatment solutions (400 nM cortisone with or without 1 μM of test molecule according to Formula (I)). After 24 h, images of migrated cells were taken using a digital camera connected to inverted microscope to observe the closure of wound area. Scratch assays were performed in quadruplicate. Results are shown in FIG. 1.

The analysis was conducted using the following compound:

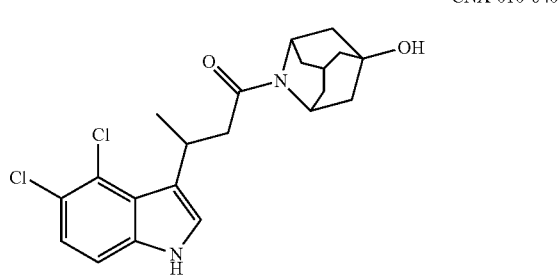

CNX-010-640

From the image analysis (FIG. 1), it is concluded that compound CNX-010-640 showed good wound healing properties.

Example 5

The following investigations were aimed at evaluating the impact of 11β-HSD inhibitor CNX-010-640, on remodeling of excision and incision wound in diet induced obese C57 mice (as a model for diabetic patients), Swiss albino mice (as a model for normal patients) and db/db mice (as a model for Type-II diabetes and obese patients).

Materials and Methods

Animal House Conditions

Animals were housed at a temperature of 22±3° C., relative humidity of 50-70%, and 12 hour light and 12 hour dark cycle. Animals were housed individually in a standard polypropylene cage with stainless steel top grill having facilities for pelleted food and drinking water in bottle. Sterile paddy husk was used as bedding material and changed every day. Pelleted mice feed was manufactured by M/s. Provimi India Pvt. Ltd. Bangalore, India or High fat diet (HFD) (D12492), 60% kcal from Fat, Research Diet (USA) was provided. Deep bore-well water passed through activated charcoal filter and exposed to UV rays in an Aquaguard on line water filter cum purifier, manufactured by Eureka Forbes Ltd., Mumbai, India was provided ad libitum. All experimental protocols were approved by the Institutional Animal Ethics Committee (IAEC) which is recognized by the Committee for the Purpose of Control and Supervision on Experiments on Animals (CPCSEA; No. 1241/bc/CPCSEA dated 5 Dec. 2008), India.

After an acclimatization period, C57 animals on the HFD were weighed and randomly allocated into different groups such as HFD cream base control and HFD+0.5% CNX-010-640 cream. C57 animals on a lean chow diet (Cream base) were also used as a control. Swiss albino mice on a lean chow diet (excision experiments only) were randomized into cream base control and 0.5% CNX-010-640 cream.

db/db Mice (from JAX lab) on chow diet were weighed and randomly allocated into different groups such as db/db cream base control and db/db+0.5% CNX-010-640 cream.

The animals were fed with their respective diets throughout the experimental period.

Excision Model

Figure 2:
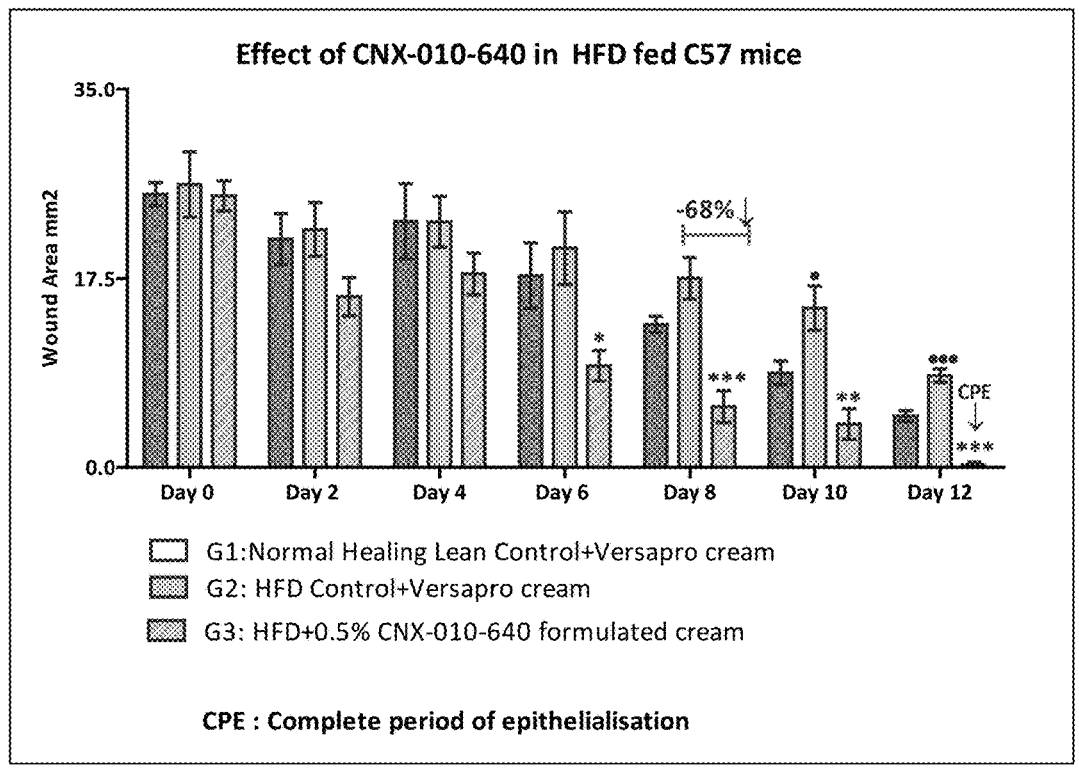
FIG. 2 shows the effect of CNX-010-640 in HFD fed C57 mice, as a model for diabetic patients. All values are presented as mean±SEM, one way ANOVA, followed by Dunnett test. n=10 until day 6 and n=5 from day 8 to day 12. p value summary: (•) <0.05, (••) <0.01, and (•••) <0.001, when compared with Normal control; and (*) <0.05, () <0.01 and (*) <0.001 when compared with HFD+ VersaPro control.
Figure 3:
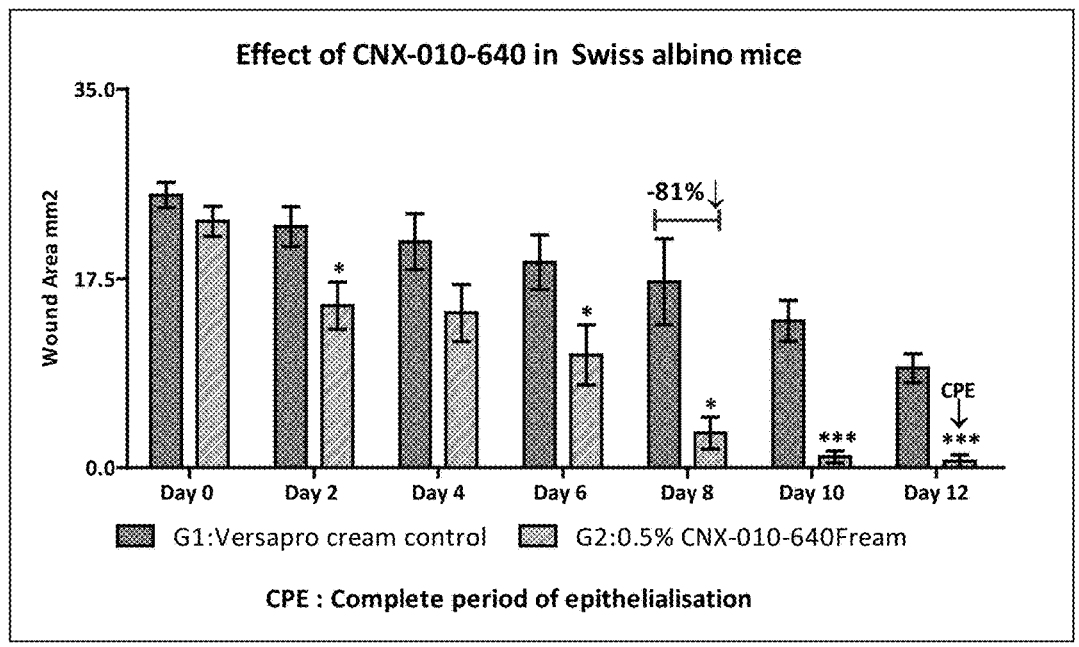
FIG. 3 shows the effect of CNX-010-640 in Swiss albino mice, as a model for non-diabetic patients. All values are presented as mean±SEM, followed by unpaired t-test. n=10 until day 6 and n=5 from day 8 to day 12. p value (*)<0.05, (***)<0.001 when compared with VersaPro control.

Mice were anaesthetized using ketamine and xylazine, hair was trimmed off and a circular excision of 20 $mm^2$ size was made on the dorsal neck region. CNX-010-640 cream was applied topically, twice a day. The degree of protection for wound remodeling was assessed by measuring wound contraction and period of epithelialisation. Wound contraction was measured on alternate days by tracing the raw wound area on graph paper carried by butter paper. Scar residue and time for completion of epithelialisation was measured. Results are shown in FIGS. 2 and 3, and Tables 1 to 3. On the termination day animals were euthanized and tissue samples containing wound was collected to study histopathological changes (as shown in FIGS. 6 to 11) and gene expression profiles were determined (FIGS. 12 to 17).

Incision Model

Figure 4:
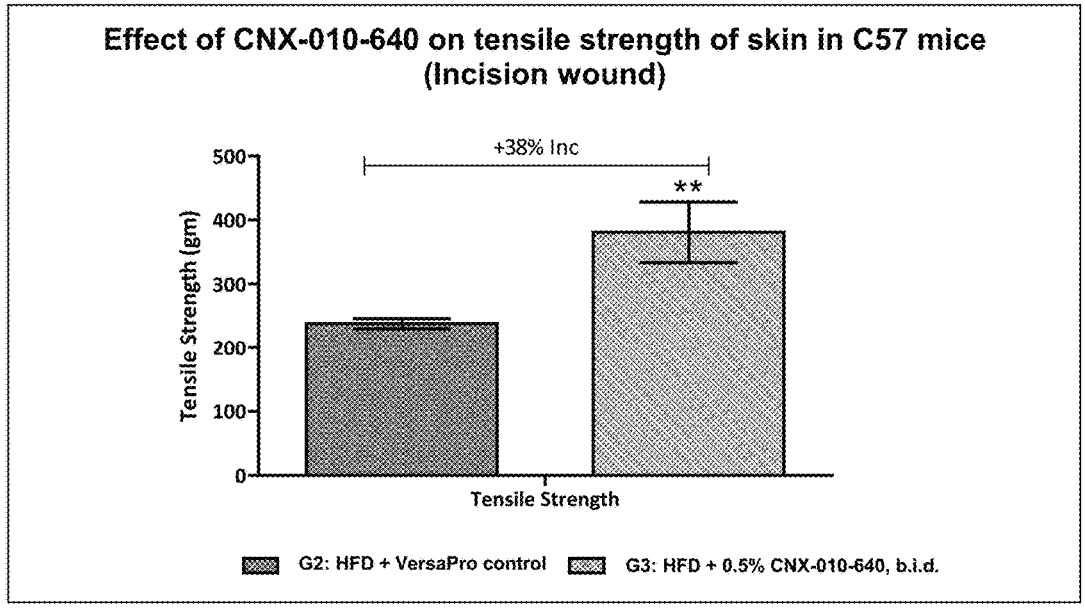
FIG. 4 shows the effect of CNX-010-640 on tensile strength of skin in diabetes-induced C57 mice after healing of an incision, compared with control mice (no active agent).
Figure 5:
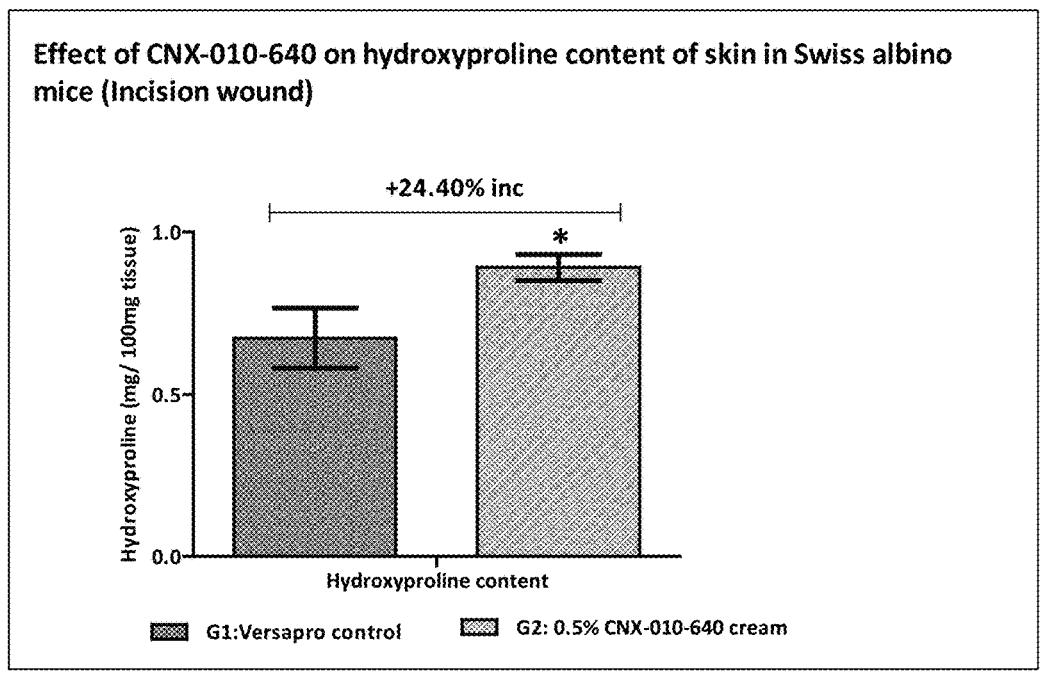
FIG. 5 shows the effect of CNX-010-640 on hydroxyproline content (as a measure of collagen content) of skin in diabetes-induced C57 mice after healing of an incision, compared with control mice (no active agent).

[6] Mice were anaesthetized using ketamine and xylazine, hair was trimmed off and a longitudinal incision of 4 to 5 cm length was made on the back and stitched with thread. CNX-010-640 cream was applied topically, twice a day. The degree of protection for wound remodeling was assessed by measuring tensile strength and collagen content of skin at the healed wound site. Wound tensile strength was measured after 14 days of treatment. Results are shown in FIGS. 4 and 5.

Statistical Analysis

[7] All the values are expressed as Mean±SEM, one way analysis of variance was performed followed by Dunnets' test for establishing the significance value of the treatment groups when compared with the HFD control.

[8] Tables 1 and 2, show results from the excision experiments.

TABLE 1

Wound contraction profile in C57 mice (in mm²)[A]

| | Groups | | |
|---|---|---|---|
| Day | G1: Normal Healing Lean Control | G2: HFD Control + VersaPro cream | G3: HFD + 0.5% CNX-010-640 formulated cream |
| 0 | 25.25 ± 1.06 | 26.14 ± 3.00 | 25.10 ± 1.40 |
| 2 | 21.13 ± 2.35 | 22.00 ± 2.47 | 15.80 ± 1.77 |
| 4 | 22.75 ± 3.48 | 22.71 ± 2.34 | 17.90 ± 1.92 |
| 6 | 17.75 ± 3.02 | 20.28 ± 3.35 | 9.40 ± 1.42 |
| 8 | 13.25 ± 0.75 | 17.50 ± 1.94 | 5.60 ± 1.47 |
| 10 | 8.75 ± 1.10 | 14.75 ± 2.05 | 4.00 ± 1.41 |
| 12 | 4.75 ± 0.47 | 8.50 ± 0.64 | 0.25 ± 0.25 |

[A]Mean ± SEM.

TABLE 2

Wound contraction profile in SAM (in mm²)[A]

| | Groups | |
|---|---|---|
| Day | G1: VersaPro cream control | G2: 0.5% CNX-010-640 formulated cream |
| 0 | 25.20 ± 1.17 | 22.77 ± 1.38 |
| 2 | 22.30 ± 1.85 | 15.00 ± 2.18 |
| 4 | 20.90 ± 2.57 | 14.33 ± 2.62 |
| 6 | 19.00 ± 2.52 | 10.44 ± 2.80 |
| 8 | 17.20 ± 3.96 | 3.20 ± 1.46 |
| 10 | 13.60 ± 1.88 | 1.00 ± 0.54 |
| 12 | 9.20 ± 1.35 | 0.600 ± 0.600 |

[A]Mean ± SEM.

[9] As can be seen from the data in Tables 1 and 2, and corresponding FIGS. 2 and 3, complete healing of the wound was achieved after 12 days when the wound was treated with CNX-010-640 in both non-diabetic Swiss albino mice (Table 2 and FIG. 3), and diabetes-induced C57 mice (Table 1 and FIG. 2). The control group wounds were not healed within this time. Furthermore, the size of wound of these control groups at the end of the experiment period (day 12) was achieved by the CNX-010-640 treated mice after only 6 days of treatment.

[10] Furthermore, as shown in FIG. 4, the tensile strength of skin at the incision site of diabetic C57 mice was markedly improved after treatment with CNX-010-640 (by up to 38%) compared with results using the control formulation.

[11] In addition, the collagen content, as estimated by measurement of hydroxyproline, was also greater in the CNX-010-640 treated diabetic C57 mice compared with controls, showing greater accumulation of connective tissue (FIG. 5).

[12] Table 3 shows the effect of treatment of CNX-010-640 on wound contraction in the db/db mouse model.

TABLE 3

Wound contraction profile in db/db mice (in mm²)[A]

| Day | G1: Normal Healing lean control | G2: db/db + Versapro cream | G3: db/db + 0.5% CNX-010-640 formulated cream |
|---|---|---|---|
| 0 | 16.25 ± 0.25 | 17.30 ± 0.90 | 17.10 ± 0.69 |
| 2 | 21.25 ± 1.49 | 27.10 ± 1.82 | 23.80 ± 0.87 |
| 4 | 16.00 ± 1.73 | 22.40 ± 1.87 | 14.40 ± 0.91 |
| 6 | 12.25 ± 0.95 | 17.00 ± 1.67 | 11.40 ± 0.48 |
| 8 | 9.25 ± 0.25 | 13.60 ± 1.17 | 8.20 ± 0.42 |
| 10 | 5.25 ± 1.38 | 10.00 ± 0.88 | 5.00 ± 0.47 |
| 12 | 1.25 ± 0.48 | 8.10 ± 0.85 | 2.20 ± 0.42 |
| 16 | 0.00 ± 0.00 | 3.20 ± 0.53 | 0.30 ± 0.21 |

[A]Mean ± SEM.

Figure 18:
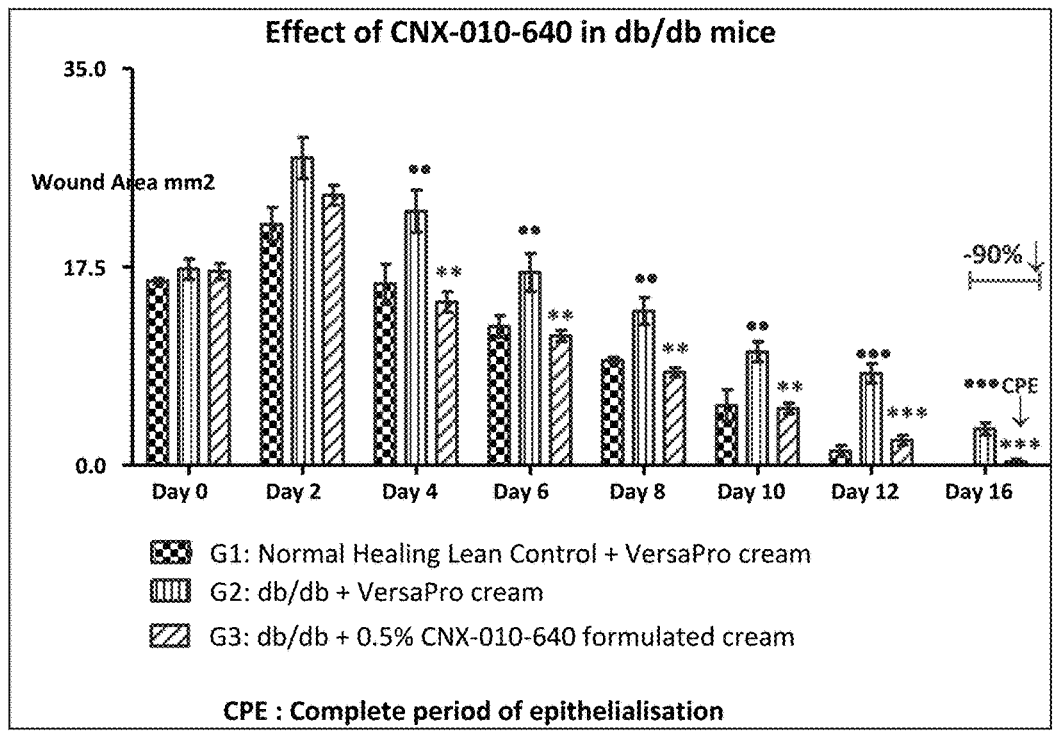
FIG. 18 shows the rate of wound healing of diabetic db/db mice when treated with or without CNX-010-640.
Figure 19:
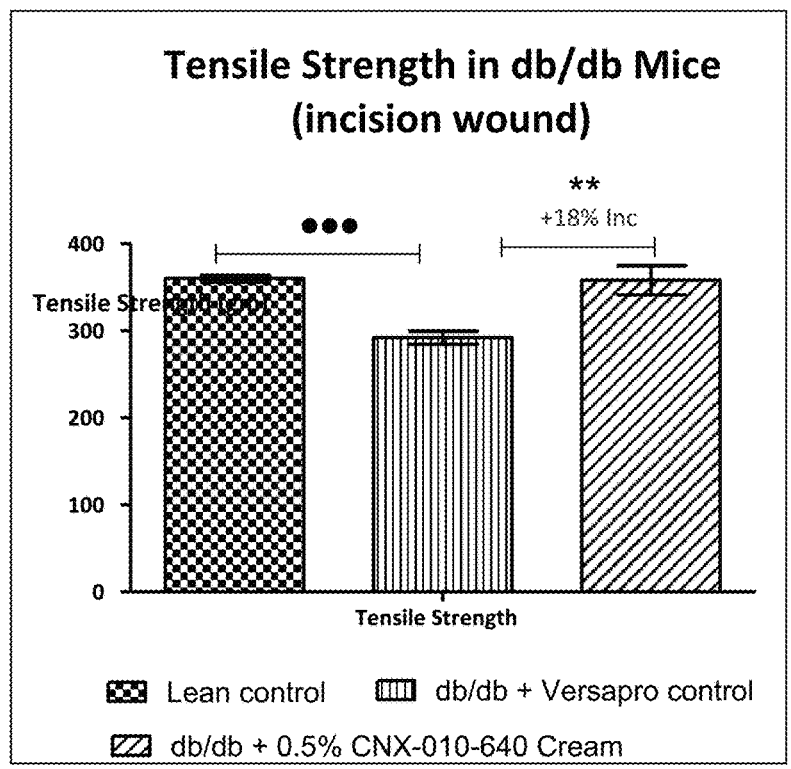
FIG. 19 shows the tensile strength of skin at the incision site of diabetic db/db mice with or without CNX-010-640.

[13] As can be seen from the data in Table 3 and corresponding FIGS. 18 and 19, complete healing of the wound was achieved after 16 days when the wound was treated with CNX-010-640 in diabetic db/db mice (Table 3 and FIG. 18). The db/db control group wounds were not healed within this time.

[14] Furthermore, the size of wound of these control groups at the end of the experiment period (day 12) was achieved by the CNX-010-640 treated mice after only 8 days of treatment.

[15] In addition, as shown in FIG. 19, the tensile strength of skin at the incision site of diabetic db/db mice was markedly improved after treatment with CNX-010-640 (by up to 18%) compared with results using the control formulation.

[16] On histopathological examination, more animals in the G3 group (HFD+0.5% CNX-010-640 formulated cream) exhibited a higher degree of fibroblast proliferation and collagen deposition (indicative of proliferative phase) in comparison with animals in G2 group (HFD+VersaPro control). See FIGS. 8 to 11.

[17] Additionally, the degree of polymorphonuclear cell infiltration (indicative of inflammatory phase) was greater in the G2 group compared to the G3 group (compare FIGS. 6 and 7).

[18] From these microscopic observations it can be concluded that the treatment with 0.5% CNX-010-640 hastened the healing process, as it facilitated an early advancement into the proliferative phase in animals treated with CNX-010-640 (G3 group) of this study.

[19] Thus CNX-010-640 cream, when applied topically b.i.d, in excision and incision wound healing model on HFD background animals and normal SAM mice, enhanced the healing process in comparison with normal healing and VersaPro control.

[20] Ex vivo studies from Excision wound model

[21] Gene expression profile

[22] After one week of compound treatment (with CNX-010-640), skin was excised near the wound area from animals (C57BL/6 mice fed on lean chow diet, on high-fat diet (HFD), and HFD with compound). The skin tissue was homogenized, total RNA was isolated using Tri-reagent (Sigma, USA) as per manufacturer's instructions and 2 µg of RNA was converted into cDNA by reverse transcription (ABI, USA) using the standard PCR method. Gene expression was measured using SYBR Green PCR Master Mix (Eurogenetic, Belgium) and relative levels of expression were quantified (see FIGS. 12 to 17).

[23] From this, it is apparent that compound treatment has reduced the markers of inflammation at the wound area, as measured by gene expression.

[24] It is understood that the foregoing detailed description and accompanying examples are merely illustrative and are not to be taken as limitations upon the scope of the invention. Various changes and modifications to the disclosed aspects will be apparent to those skilled in the art. Such changes and modifications, including without limitation The claims defining the invention are as follows:

1. A method of treating a wound, comprising administering to a subject in need thereof a therapeutically effective amount of a compound of Formula (I), or a pharmaceutically acceptable salt thereof:

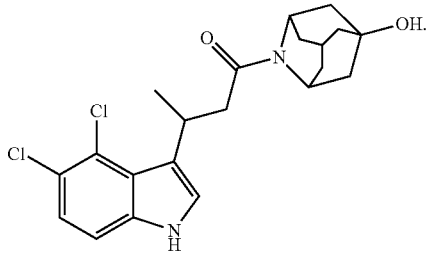 [SMILES: CC(CC(=O)N1C2CC3CC1CC(O)(C3)C2)c1c[nH]c2ccc(Cl)c(Cl)c12]

2. The method according to claim 1, wherein the wound is an incision or an excision.

3. The method according to claim 1, wherein the compound is administered topically to the site of the wound.

4. The method according to claim 1, wherein the compound is administered in the form of a balm, a cream, a gel, a liniment, a lotion, an ointment, a paste, a rub or a salve.

5. A compound of Formula (I), or a pharmaceutically acceptable salt thereof for use in treating a wound in a subject:

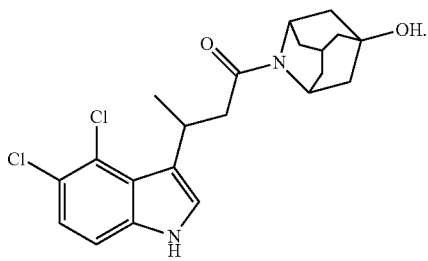 [SMILES: CC(CC(=O)N1C2CC3CC1CC(O)(C3)C2)c1c[nH]c2ccc(Cl)c(Cl)c12]

6. The compound for use according to claim 5, wherein the wound is an incision or an excision.

7. The compound for use according to claim 5, wherein the compound is administered topically to the site of the wound.

8. The compound for use according to claim 5, wherein the compound is administered in the form of a balm, a cream, a gel, a liniment, a lotion, an ointment, a paste, a rub or a salve.

9. A method according to claim 1 wherein the compound of Formula (I) or a pharmaceutically acceptable salt thereof is administered in the form of a pharmaceutical composition, wherein the pharmaceutical composition comprises a compound of Formula (I) as described in claim 1, or a pharmaceutically acceptable salt thereof, and a pharmaceutically acceptable diluent, excipient or carrier.

10. The method according to claim 9, wherein the pharmaceutical composition comprises from 0.1 to 2% (w/w) of a compound of Formula (I), or a pharmaceutically acceptable salt thereof and from 99.9 to 98% (w/w) of a carrier.

11. The method according to claim 10, wherein the compound, or a pharmaceutically acceptable salt thereof, is present in the pharmaceutical composition in the range of 0.1 to 1% (w/w), and the carrier is present in the range 99.9 to 99% (w/w).

12. The method according to claim 11, wherein the compound, or a pharmaceutically acceptable salt thereof is present in the pharmaceutical composition at about 0.5% (w/w), and the carrier is present at about 99.5% (w/w).

13. The method according to claim 10, wherein the pharmaceutical composition comprises 0.1 to 2% (w/w) of a compound of Formula (I), or a pharmaceutically acceptable salt thereof; one or more emollients at about 5 to about 10% (w/w); one or more surfactants at about 10 to about 15% (w/w); one or more humectants at about 1 to about 10% (w/w); one or more preservatives at about 1 to about 5% (w/w); one or more antioxidants at about 0.1 to about 2% (w/w); and a solvent making the remaining balance up to 100% (w/w).

14. The method according to claim 13, wherein the one or more emollients is selected from the group consisting of heavy liquid paraffin, kokum butter and cetyl alcohol.

15. The method according to claim 13, wherein the one or more surfactants is selected from the group consisting of glyceryl monostearate, stearic acid, polyethylene glycol, cetostearyl alcohol and ethylene glycol monostearate.

16. The method according to claim 13, wherein the one or more humectants is glycerine.

17. The method according to claim 13, wherein the one or more preservatives is selected from the group consisting of phenoxy ethanol, potassium sorbate and sodium benzoate.

18. The method according to claim 13, wherein the one or more antioxidants is vitamin E.

19. The method according to claim 13, wherein the solvent is water.

20. The method according to claim 9 wherein the pharmaceutical composition comprises 0.5% (w/w) of a compound of Formula (I), or a pharmaceutically acceptable salt thereof; heavy liquid paraffin—2.5% (w/w); glyceryl mono stearate—1.85% (w/w); stearic acid—2.0% (w/w); kokum butter—2.0% (w/w); polyethylene glycol—5.0% (w/w); glycerine—5.0% (w/w); cetostearyl alcohol—2.5% (w/w); cetyl alcohol—2.0% (w/w); ethylene glycol monostearate—1.0% (w/w); phenoxy ethanol—0.5% (w/w); potassium sorbate—0.5% (w/w); sodium benzoate—0.5% (w/w); vitamin E—0.5% (w/w); and purified water—73.65% (w/w).

* * * * *